(12) United States Patent
Franzen et al.

(10) Patent No.: US 8,142,996 B2
(45) Date of Patent: Mar. 27, 2012

(54) MASS SPECTROMETRIC DETERMINATION OF BLOOD ENZYME ACTIVITY

(75) Inventors: Jochen Franzen, Bremen (DE); Karsten Michelmann, Harpstedt (DE); Markus Kostrzewa, Taucha (DE)

(73) Assignee: Bruker Daltonik GmbH, Bremen (DE)

( * ) Notice: Subject to any disclaimer, the term of this patent is extended or adjusted under 35 U.S.C. 154(b) by 694 days.

(21) Appl. No.: 12/224,388

(22) PCT Filed: Feb. 15, 2007

(86) PCT No.: PCT/EP2007/001299
§ 371 (c)(1),
(2), (4) Date: Mar. 3, 2009

(87) PCT Pub. No.: WO2007/098859
PCT Pub. Date: Sep. 7, 2007

(65) Prior Publication Data
US 2009/0305327 A1    Dec. 10, 2009

(30) Foreign Application Priority Data
Feb. 28, 2006   (DE) .................... 10 2006 009 083

(51) Int. Cl.
*C12Q 1/00* (2006.01)
*G01N 33/49* (2006.01)
(52) U.S. Cl. ............................. 435/4; 436/86
(58) Field of Classification Search .................. None
See application file for complete search history.

(56) References Cited

U.S. PATENT DOCUMENTS

| 6,881,586 | B2 * | 4/2005 | Hutchens et al. | 506/5 |
| 7,893,616 | B2 * | 2/2011 | Wu et al. | 313/564 |
| 2002/0137106 | A1 * | 9/2002 | Leung et al. | 435/7.9 |
| 2004/0223880 | A1 * | 11/2004 | Gjerde et al. | 422/70 |
| 2006/0160167 | A1 | 7/2006 | Elased | |

FOREIGN PATENT DOCUMENTS

| WO | WO 03/102222 | 12/2003 |
| WO | WO 2004/005918 | 1/2004 |
| WO | WO 2004/029286 | 4/2004 |

OTHER PUBLICATIONS

Khalid M. Elased, David R. Cool, Mariana Morris, "Novel Mass Spectrometric Methods for Evaluation of Plasma Angiotensin Converting Enzyme 1 and Renin Activity", Hypertension 2005; 46; 953-959.

Xinfeng Zhou, Frantisek Turecek, C. Ronald Scott, Michael H. Gelb, "Quantification of Cellular Acid Sphingomyelinase and Galactocerebroside β-Galactosidase Activities by Electrospray Ionization Mass Spectrometry", Clinical Chemistry 47, 5, 874-881 (2001).
Jing Su, Michelle R. Bringer, Rustem F. Ismagilov, Milan Mrksich, "Combining Microfluidic Networks and Peptide Arrays for Multi-Enzyme Assays", J. Am. Chem. Soc. 2005, 127, 7280-7281.
Yijun Li, C. Ronald Scott, Nestor A. Chamoles, Ahmad Ghavami, B. Mario Pinto, Frantisek Turecek, Michael H. Gelb, "Direct Multiplex Assay of Lysosomal Enzymes in Dried Blood Spots for Newborn Screening", Clinical Chemistry 50:10, 1785-1796 (2004).
Dieter Drexler, Deborah J. Barlow, Paul Falk, Joseph Cantone, Dennis Hernandez, Asoka Ranasinghe, Mark Sanders, Bethanne Warrack, Fiona McPhee, Development of an on-line automated sample clean-up method and liquid chromatography-tandem mass spectrometry analysis: application in an in vitro proteolytic assay Anal Biononal Chem. (2006) 384: 1145-1154.
André Liesener, Uwe Karst "Monitoring enzymatic conversions by mass spectrometry: a critical review", Anal Bioanal Chem. (2005) 382:1451-1464.
Liotta Lance A. et al. "Serum peptidome for cancer detection: spinning biologic trash into diagnostic gold." The Journal of Clinical Investigation Jan. 2006, vol. 116, No. 1, Jan. 2006, pp. 26-30.
Gygi S.P. et al. "Quantitative analysis of complex protein mixtures using isotope-coded affinity tags". Nature Biotechnology, Nature Publishing Group, New York, NY, US, vol. 17, No. 10, Oct. 1999, pp. 994-999.
Pan Sheng et al. "High throughput proteome screeing for biomarker detection". Molecular & Cellular Proteomics : MCP Feb. 2005, vol. 4, No. 2, Feb. 2005.
Villanueva Josef, et al. "Differential exoportease activities confer tumor-specific serung peptidome patterns". The Journal of Clinical Investigation Jan. 2006, vol. 116, No. 1, Jan. 2006, pp. 271-284.

* cited by examiner

*Primary Examiner* — Nashaat Nashed
(74) *Attorney, Agent, or Firm* — Paul Vincent

(57) ABSTRACT

The invention relates to the determination of the nature and strength of enzymatic activity in blood using mass spectrometric measurement of a profile of the reaction products. The determination of the enzymatic activity can be used for medical diagnostics, for example, and also to check the effectiveness of medication. The invention provides a method whereby adding probe substances usually not present in blood offers standardized substrates for measuring the enzymatic activity. The probe substances may be added to whole blood, plasma, or serum. The mass spectrometric measurement of the reaction products, after their reversible immobilization on actively binding surfaces of solids, for example, can deliver biomarker patterns of the reaction products which may be indicators for metabolic anomalies or diseases, since these are often accompanied by the formation or activation of characteristic enzymes.

20 Claims, No Drawings

MASS SPECTROMETRIC DETERMINATION OF BLOOD ENZYME ACTIVITY

This application is the national stage of PCT/EP2007/001299 filed on Feb. 15, 2007 and also claims Paris Convention priority to DE 10 2006 009 083.7 filed on Feb. 28, 2006.

BACKGROUND OF THE INVENTION

The invention relates to the determination of the nature and strength of enzymatic activity in blood using mass spectrometric measurement of a profile of the reaction products. The determination of the enzymatic activity can be used for medical diagnostics, for example, and also to check the effectiveness of medication.

The invention provides a method whereby adding probe substances usually not present in blood offers standardized substrates for measuring the enzymatic activity. The probe substances may be added to whole blood, plasma, or serum. The mass spectrometric measurement of the reaction products, after their reversible immobilization on actively binding surfaces of solids, for example, can deliver biomarker patterns of the reaction products which may be indicators for metabolic anomalies or diseases, since these are often accompanied by the formation or activation of characteristic enzymes.

In a recent publication "Differential exoprotease activities confer tumor-specific serum peptidome patterns", J. Villanueva et al., J. Clin. Invest., 116: 271-284 (2006), it was explained that the digest peptides in blood, which have been known for a long time, are not just useless trash, as had largely been assumed, but that it was possible to identify characteristic patterns therein for the identification of disease-specific enzyme activities. The authors were able to use the digest peptide patterns of endogenous blood proteins which are present in high concentrations, such as fibrinogens or other clotting factors, to distinguish between three different types of cancer as well as healthy control samples. They coined the name "serum peptidome" for the pattern of the peptides present in blood. The paper was held to be so sensational that two famous specialists in the field wrote a long accompanying comment: "Serum peptidome for cancer detection: spinning biologic trash into diagnostic gold", L. A. Liotta and E. F. Petricoin, J. Clin. Invest., 116: 26-30, 2006.

After broadband extraction by superficially hydrophobic magnetic beads, the digest peptides were measured in a MALDI mass spectrometer, i.e. with ionization by matrix-assisted laser desorption; the peptides extracted from a sample in this way can be recorded in a single mass spectrum. The analysis of these breakdown products shows that the breakdown reactions of the proteins by the enzymes in the blood did not proceed in the same way in all blood samples but rather the nature and speed of the reactions differed depending on the disease. Moreover, the paper confirmed that not all proteins in the blood are broken down. Practically no digest peptides of the most prevalent proteins, i.e. the albumins and globulins, can be found. These high-molecular proteins are protected by their structure in such a way that they resist enzyme attack. The digest peptides could be mostly assigned to the clotting factors such as fibrinogen α or C3f.

Mass spectrometric diagnostics carried out by measuring and evaluating mass spectra obtained from substance mixtures extracted from body fluids is still in its infancy. This is true for both the development of the measurement and evaluation methods as well as for the licensing of the mass spectrometers for diagnostic purposes. The first mass spectrometers which are licensed for medical diagnostics are now coming onto the market. In Europe, the licensing is effected by means of a manufacturer's IVD declaration of conformity (CE), which is strictly monitored by official bodies. The abbreviation IVD stands for "in vitro diagnostics". In Germany, this licensing is regulated by the Medical Devices Act (MPG), which is based on the European Directive 98/79/EC. Outside Europe there are usually regulations which require licensing by official bodies.

A particularly promising diagnostic method is one which measures protein mixtures extracted from body fluids, especially blood. The mass spectra of the protein mixtures are often simply called "protein profiles". Blood is routinely taken from a vein in all general practices; the risk from side effects is very low. The risk is even smaller when only one drop of blood is taken from the fingertip or earlobe.

In the protein profiles from the blood, significant over- and underexpressions of specific proteins can be measured, which are reflected in concentrations that are too high or too low. It is also possible to measure chemical changes in proteins, which then appear with a different molecular weight at other points in the mass spectrometric protein profile. Statistically significant changes of this nature are always an indication of a specific stress situation of the body, and in some cases are even characteristic of a specific disease of bodily organs or of a metabolic anomaly. Such proteins which undergo characteristic changes in their concentration or molecular weight as a result of stress are now termed "biomarkers". The term "biomarker" increasingly refers not just to an individual protein, but rather to a pattern of several proteins or protein derivatives which characteristically change in terms of their concentration ratio to each other. In a wider sense, it does not have to be a protein profile; it can also be a mass spectrum of any extracted substance mixture from which biomarkers can be obtained. Measurements of such biomarkers or biomarker patterns can be used to medically diagnose diseases, metabolic anomalies or the response to medication, and also for many more purposes, from the explanation of breakdown pathways in metabolomics through to pharmacokinetic analyses in the development of new drugs. After all, biomarker patterns are not only to be found in blood, but also in any body fluids including lyzed tissue, even if the focus of attention here is especially on blood samples.

Blood consists mainly of water (over 90%), various types of blood particles, small amounts of salts, several non-protein organic substances, and around seven percent is made up of proteins, of which albumins and globulins form the largest part. The next most prevalent are the so-called clotting factors, above all the fibrinogens. The general term "blood samples" below can mean "whole blood", "blood serum" or "blood plasma"; the differences are explained in more detail below. The proteins which are of interest here as possible biomarkers are present in the blood samples at concentrations of less than one percent down to $10^{-10}$ percent. The proteins present in very low concentrations elude direct measurement if they cannot be especially "fished out" in a substance-specific way or indirectly measured by the effects they cause. One type of such indirect measurement by an enzymatic effect has already been described in detail above.

If the blood particles are removed from blood which has just been taken (the "whole blood") by centrifuging, for example, then the "blood plasma" is obtained, which still contains all the clotting factors, above all the fibrinogens. If it is to be stored for a long period or transported, the blood plasma must be prevented from coagulating by adding anticoagulants. If, on the other hand, the whole blood is coagulated, the fibrinogens are broken down to fibrins through different stages with the assistance of the other clotting factors. These fibrins polymerize and together with the blood corpuscles form the blood clot. If this blood clot is removed by centrifuging, one obtains the "blood serum", which now contains (almost) no coagulants.

In a good mass spectrometer, a hundred attomols of a protein (60 million molecules) can still provide a measurable signal; but in a protein profile with its background noise, this detection limit is higher because of an unavoidable background noise; it is around a hundred femtomoles.

For a peptide with a molecular weight of 1,000 Daltons, this corresponds to a hundred picograms, and to one nanogram for a protein with a molecular weight of 10,000 Daltons. Thus, in a small drop of blood containing only ten microliters of blood (ten milligrams), proteins down to a concentration of $10^{-5}$ percent by weight can be measured if it proves possible to feed all the proteins of interest to the measurement and to measure a protein profile which is not completely overloaded with proteins. Close to the detection limit, however, the accuracy of the measurement is not very good, so direct measurement and evaluation of the protein profiles is today generally limited to the concentration range between $10^{-1}$ and $10^{-3}$ percent by weight.

The smaller proteins with molecular weights of up to several thousand Daltons, which consist of only a few tens of amino acids, are called peptides; unless otherwise specifically mentioned, they are included here in the term "proteins", however. The definition line between peptides and proteins is very unclear. The vast majority of peptides in the blood are so-called "digest peptides", which are created as a result of the continuous enzymatic breakdown of larger proteins, which is sometimes stronger and sometimes weaker, for example the breakdown of fibrinogens, but also of foreign proteins. Until very recently, these digest peptides (the "peptidome") were considered to be "trash" which contained no information about the state of the body.

In the paper cited above it was demonstrated, however, that characteristic patterns of peptides can be measured in blood, each indicating the activity of particular enzymes. The catalytic activity of these enzymes is principally directed at the fibrinogens and other clotting factors as substrate and breaks these down in various stages in conjunction with endopeptidases and exopeptidases to give digest peptides which, through the action of the exopeptidases, are present in part as digestion ladders of various lengths. In keeping with their task, the clotting factors are neither particularly stable nor particularly protected, and hence easily accessible to enzymatic breakdown. The activities of the enzymes measured indirectly on the basis of the nature and strength of the digest peptides were, in turn, unambiguously assigned to specific types of cancer. It was possible to detect the patterns of these digest peptides not only in the whole blood but also in the blood serum and blood plasma. The enzymes themselves eluded mass spectrometric measurement because of their very low concentration; they only revealed themselves through the reaction products of their catalytic activity. These peptide patterns can thus indeed serve as biomarkers. This indirectly extends the concentration range which is available for biomarker measurements to specific types of enzymes and increases it by several powers of ten for these enzymes.

Endo-peptidases cut proteins at certain enzyme-specific points in the middle of the amino acid chain of the proteins. One example of this is the familiar digest enzyme trypsin, which cuts adjacent to the amino acids lysine and arginine respectively. The motif at which a specific enzyme cuts can consist of a specific amino acid or a short chain of several amino acids. Exopeptidases, on the other hand, break down peptides from the end: one amino acid after the other is removed, generally creating a mixture of digest peptides of different lengths, the difference between them being one amino acid, which enables the sequence of the broken down peptides to be identified in a mass spectrometric measurement by the mass differences. Exopeptidases work from either the C-terminal or the N-terminal end of the peptide, not from both ends at the same time. The mixtures of breakdown products created by exopeptidases are also called "digestion ladders".

All enzymes have a catalytic effect on other substances, which are termed the "substrate" of the enzyme, and which are modified by the catalytic activity of the enzyme in a way which is characteristic of that enzyme. The enzymes are therefore not used up through their activity, but rather their activity gradually decreases over quite long periods of some days; the activities of other enzymes or even self-digestion also play a part. The half lives of the enzymes' activity are a few days; freezing prevents the activity from diminishing. The speed of the catalytic reactions, and hence the speed of modification of the substrates, varies greatly. "Sluggish enzymes" have a reaction rate of around one substrate molecule per second and enzyme molecule; fast enzymes can exhibit a reaction rate of up to 100,000 substrate molecules per second and enzyme molecule. The fastest known enzyme is catalase, which breaks down hydrogen peroxide, which is toxic to the body. A fast reaction rate requires that sufficient substrate molecules are available, however, and also that diffusion does not cause a restriction. The peptidases, which digest proteins and peptides, have reaction rates of around 100 to 1,000 substrate molecules per second and enzyme molecule.

The number of different types of protein in the blood is extremely high, far above 100,000. Even in the narrow concentration range for the direct measurement of the protein profiles there are many thousands of proteins. A mass spectrum with such a large number of proteins would not enable an individual protein to be identified because the mass spectrometric signals would produce unresolved superimpositions. It is therefore necessary to drastically reduce the number of proteins before measuring a protein profile, yet still provide a large number of proteins for the measurement. This is generally done by means of broadband extractions, which are able to extract proteins which share specific properties from the blood. Such broadband extractions can simultaneously extract several tens to several hundreds of proteins whose concentrations are in the measurable range. The term "broadband extraction" should not be interpreted too narrowly here, however; extractions which, for example, extract only two proteins for a determination of their concentration ratio in a reproducible way should also be understood as being covered by the term broadband extraction.

There are different types of broadband extraction, different with respect to "what" (types of protein extracted) as well as to "how" (extraction mechanism). Reversible immobilization of proteins on suitable actively binding surfaces of solids is the easiest extraction mechanism to work with. It is the only one considered here. The actively binding surfaces of solids are generally produced by stably coating the surfaces of the solids with suitable substances.

The different modes of operation of broadband extractions are distinguished by actively binding surfaces of solids which have different coatings; they extract completely different types of protein out of the blood sample. The proteins can be bound to the surface by means of electric interactions, for example, by stably coating the surfaces with anion or cation exchangers. This extracts proteins with different ionic charges from the blood. Other proteins can be affinely bound via hydrophobic bonds, as occurs in reversed phase chromatography. Other types of protein again can be held on the surface by means of various chelate-type bonds, by substance-specific ligand bonds, and also by customized, protein-specific bonds along the lines of the antigen-antibody bond. This means that a mixture of different types of antibodies stably bound to the surfaces of solids can also extract a protein profile.

Different types of broadband extraction usually produce totally different protein profiles because quite different types of proteins are extracted by reversible immobilization on the surface of the solids in each case. Patterns of characteristic biomarkers can also be composed of signals in different types of protein profiles; they therefore do not need to originate from a single protein profile.

Digest peptides are generally extracted by hydrophobic surfaces. C8 and C18 surfaces, in particular, have proven to be successful here. These surfaces are covalent bonds of alkanes with 8 or 18 carbon atoms (generated by "alkylation"). If the digest peptides have some non-polar amino acids in their chain, then they are reversibly bound here. These hydrophobic coating layers are also called reversed phases. Ferromagnetic particles (magnetic beads) with such coatings are commercially available.

The actively binding surfaces for this broadband extraction can belong to different types of solids. The vessel walls of the sample containers can themselves be actively coated, or actively binding sampling spots can be located on special sample supports. The coatings must be stably, i.e. irreversibly, bound. The samples can be forced through actively binding filter material in the form of felt, open-pored foams or particle-filled cavities. Macroscopic beads or pellets, or suspensions of microparticles or nanoparticles with actively binding surfaces can be added to the liquid sample and later recovered from the sample liquid together with the immobilized extraction substances by filtration, centrifuging or magnetic forces. The extraction substances can be washed in the immobilized state on the surface of the solid and hence freed of all other substances. The immobilized extraction substances can then be released again where and when necessary by suitable eluents.

The above-described indirect measurement of the enzyme activity in blood with the aid of the resulting reaction products is a breakthrough for the diagnostic application of biomarkers, but also has its disadvantages. Alone the changing composition of the blood proteins which can be used for a digestion, and other problems as well, mean that analysis of the digest peptides cannot be standardized very well. It has turned out, for example, that some clotting factors in the blood of patients with certain diseases were not present in measurable quantities at all because they had already been completely digested in the patient's body. In the paper cited, the researchers were able to prove that adding such clotting factors, for example fibrinogen β, leads to a breakdown in seconds. Furthermore, there are always some enzymes in the blood which continuously lead to breakdown products so that it is sometimes difficult to distinguish between these and disease-specific enzymes.

A further problem of carrying out diagnostics with the aid of digest peptides from blood samples is the undesired, continuous change during storage and transportation. Blood is a long-lastingly reactive fluid; the enzymes it contains do not lose their effectiveness when a blood sample is taken. It is not just that proteins are digested or changed in a characteristic way; chemical processes such as oxidation are also frequently enzyme-controlled. Equilibria which have formed in the blood circulation are disturbed in the blood sample taken.

Another consideration is clotting, caused by the conversion of fibrinogens into fibrous fibrin, which is also controlled by enzymes such as thrombin. Thrombin is formed by the decomposition of the platelets, which are a type of small blood particle. The speed of change of the proteins in blood depends on many factors. For example, the temperature of the sample is important, as is its state of motion, the oxygen content, and the individual composition of the blood itself. Blood must therefore always be stabilized for transportation or storage. This causes problems when the samples have to be transported from the location where the blood is taken (usually a doctor's practice) to the place where the mass spectrometric measurement is carried out.

Freezing the whole blood sample, the blood serum or the blood plasma at minus 80° C. (−112° F.) has therefore established itself as the best type of stabilization method, but it can only be carried out in a small number of doctor's practices, and usually only in hospitals. Carriers who specialize in refrigerated transportation have to be used to transport the blood over long distances, making the transportation expensive.

The objective of the invention is to provide methods for determining enzyme activities in blood.

SUMMARY OF THE INVENTION

The invention is described by the independent method claim. Favorable embodiments are given by the dependent method claims. The remaining claims recite applications (uses) of the determination method.

The invention consists in adding specified quantities of one or more exogenous probe substances to whole blood, blood plasma or blood serum, subjecting these added probe substances, as substrates, to the catalytic reactions of the enzymes in the blood under specified conditions, then extracting some or all reaction products and measuring them so as to be able to identify and quantify them. It is preferable to use mass spectrometric measurement since this enables a large number of reaction products to be recorded in a single measurement. It is favorable if the structure of the probe substances is precisely known.

The probe substances should be exogenous, i.e. they should not be present in the blood, at least not in concentrations which can be measured mass spectrometrically. The use of such probe substances then makes it possible to standardize the method with precisely specified reaction parameters such as temporal addition profile, temperature, reaction time and motion, for example by means of a specified incubation time at a specified temperature after a one-off addition of the probe substances. It particularly makes it possible to relate the reaction products to the probe substances added. The probe substances do not have to be added all at once, however; it can be more favorable to specifically spread the addition over quite a long period since, in this case, all intermediate products of the enzymatic activity can be measured in parallel.

In addition to the probe substances, it is also possible to add auxiliary substances which affect the activity of the enzymes, for example by forming coenzymes.

Foreign proteins especially can be used as probe substances, but also other substances which are changed by enzymatic action. The reactions of the probe substances catalytically induced by enzymes can consist in a breakdown by hydrolases, for example by exopeptidases or endopeptidases, and also in a conversion, for example by transferases or oxidases.

"Foreign proteins" should be taken here to mean all types of exogenous proteins, for example synthesized proteins, or protein-like substances which can be created by modifications to exogenous natural or synthesized proteins, including the incorporation of artificial amino acids into synthesized proteins. The foreign proteins can be pure amino acid chains or versions thereof modified in a wide variety of ways. It is preferable if the probe substances used here are foreign proteins. The term "exogenous proteins" should be taken to mean proteins whose sequences do not resemble the endogenous proteins (excluding the globulins and albumins, which are practically impossible to break down) that are present in high concentrations in the blood, so that their digest peptides or other kinds of reaction products can be unambiguously assigned to the foreign proteins added. The term "artificial amino acids" should be taken to mean amino acids which demonstrate the fundamental structure of amino acids but which are not any of the 20 known amino acids that are almost exclusively to be found in living nature. It is also possible to use isotope-marked substances.

The extraction of all or a large number of reaction products can preferably be carried out by immobilization on actively binding surfaces with subsequent washing; extraction and washing also bring the enzymatic activity to an end. Broadband extractions by reversible immobilization on actively binding surfaces of solids are very simple to carry out. Digest peptides can be bound particularly well to the surfaces of particles which are coated with C8 or C18 reversed phases.

Particularly favorable are specific extractions of reaction products with the aid of anchor groups to modify the probe substances since, in this case, the extraction is restricted to reaction products of the probe substances. These anchor groups can enable a targeted extraction of the reaction products by suitable immobilized capture substances. For example, biotin groups of the probe substances can be bound to immobilized streptavidin in the familiar way.

The anchor groups can reversibly bind to the capture substances, or they can be bound by means of photolytically or chemolytically cleavable linkers so that the extracted foreign proteins can be released again after the extraction. Such cleavable linkers can also be located inside the amino acid chain of the foreign proteins so that partial chains can also be cleaved off.

The modifications of the foreign proteins can exist in many types of chemical group which are covalently bound to the foreign protein. The covalently bound chemical groups can themselves contribute to special cleavage reactions by the enzymes, such as phosphorylations or sulfations.

The modifications can especially be maskings of the C terminus or N terminus in order to protect the proteins from being broken down from the ends by exopeptidases. The specialist is familiar with maskings of this type. This type of breakdown by exopeptidases can thus only occur when an endopeptidase has caused the protein used to be cut open at a location which is characteristic for the enzyme. The endopeptidases lead to very characteristic fragments of the foreign proteins used; the exopeptidases then create digestion ladders of these fragments. By incorporating artificial amino acids, the breakdown by exopeptidases can be controlled to a great extent; for example it can be stopped when a minimum length is reached. The proteins added can not only be broken down, they can also be chemically modified, for example oxidized, under enzymatic control.

Ready made vessels for the broadband extractions mean that the whole procedure can be carried out in the doctor's practice as soon as the blood has been taken; the extracted proteins can be sent to the mass spectrometry laboratory at normal temperature in a cleaned and immobilized state.

The immobilized state prevents the proteins from undergoing further reactions with each other, even if enzymes are immobilized as well in the process.

DESCRIPTION OF THE PREFERRED EMBODIMENT

Enzymes act in a characteristic way catalytically on specific substrates and modify them, creating specific reaction products. With knowledge of the substrates and the reaction products it is possible in many cases to draw unambiguous conclusions as to the identity of the enzymes. These enzymes can thus be indirectly measured by the reaction products from known substrates; depending on the duration and rate of the reaction, the molecules of the reaction products can be many orders of magnitude more prevalent than the enzyme molecules. If, for example, a peptidase molecule brings about the cleavage of the molecules of a certain protein at a rate of 140 protein molecules per second, then after only ten minutes there are already 100,000 cleavage product molecules per enzyme molecule. This reaction rate is not even high, but rather below average. The prerequisite, however, is the supply of a sufficiently large number of substrate molecules, which have to be present in a very high concentration in order not to bring about any limitation of the activity due to diffusion.

If, therefore, certain enzyme molecules are present in the blood at a concentration of only $10^{-6}$ percent, and a suitable substrate is added at a concentration of around one percent, then after only ten minutes incubation time reaction products at a concentration of around one tenth of a percent will be present. This concentration is ideal for broadband extraction with subsequent mass spectrometric determination. The reaction rate of the substrates as a result of the enzymes is strongly dependent on the temperature; most enzymes work best at 37 (approx. 99° F.), i.e. at body temperature. A temperature which Is around five to ten degrees Celsius 41° F.-50° F.) lower reduces the reaction rate by around half.

To identify diseases, the reaction products of widely different types of enzyme can serve as biomarkers. Different types of peptidases are suitable for identifying different types of cancer, for example. In this case it is favorable to use modified foreign proteins as the probe substance on which the peptidases can act. We will restrict ourselves in the following to the addition of such foreign proteins, although this should not mean that the invention is restricted to such probe substances. It should also particularly be noted that knowledge of the enzymes is not necessary for the method as long as their activity can be assigned to specific diseases or anomalies on the basis of the reaction products.

Any development of a diagnostic method which is based on biomarkers generally starts with scientific research to find biomarker patterns in measured protein profiles. In the case of this invention, the search relates not only to significantly different characteristic patterns in the mass spectra of the samples from sick and healthy persons, as is the case with a normal biomarker search, but rather here it is also necessary to find favorable probe substances which can be used as substrates of the enzymatic activity. To apply the invention it is thus necessary to also search for suitable probe substances to determine disease-specific enzyme activities. The biomarker search here has a further dimension: the search for suitable probe substances. Below we therefore describe both the search for suitable probe substances, the search for biomarkers in the reaction products, and the diagnostic use.

Since our focus of attention here is the use of foreign proteins as probe substances, we first describe the determination of sequences for foreign proteins and their manufacture. According to the above definition, the foreign protein should not resemble any of the blood proteins which are present in high concentrations (with the exception of globulins and albumins).

Simple combinatorial analysis makes it possible to calculate that with 20 amino acids there are some 3.2 million different types of sequence pentuplets, i.e. sequence segments each having a length of five amino acids. The sequence pentuplets encompass all combinations of five amino acids with the possibility that an amino acid can occur repeatedly, and taking into account their position in the sequence pentuplet. If one now combines high concentration proteins in order of decreasing concentration until their chain lengths added together amount to some two million amino acids (this encompasses all proteins present in high concentrations), then this quantity of proteins contains a maximum of two million different types of (overlapping) sequence pentuplets. The sequences of the proteins present in the blood in high concentrations are all known and can be obtained from databases. Suitable computer methods thus make it possible to determine all sequence pentuplets present in the blood in high concentrations. This leaves over a million sequence pentuplets which do not occur in the proteins present in high concentrations and which can easily be determined as what is left of all the sequence pentuplets after all known sequence pentuplets of the proteins present in high concentrations have been subtracted.

From these now known sequence pentuplets which are foreign to the blood, it is easy to compose protein sequences, each around 20 to 40 amino acids in length, whose overlapping sequence pentuplets do not occur in any of the proteins present in high concentrations in the blood. Many thousands of such protein sequences can be determined. It is even possible to choose whether the amino acids here are to be uniformly distributed or whether certain amino acids are to be primarily incorporated. (All living things have amino acids which primarily occur). Moreover, mathematical algorithms can be used to determine whether the foreign proteins so determined will primarily be present in strongly folded, weakly folded or largely unfolded form. The foreign proteins with different degrees of folding possess different resistances to enzymatic breakdown. The experienced biochemist can draw on his experience of enzymatic breakdown to determine a selection of ten to a hundred such foreign proteins which will be suitable for determining a disease-specific breakdown.

The specialist is familiar with how to synthesize any proteins with known sequence. There are methods of direct chemical synthesis and also recombinatory biosynthesis with the aid of synthesized DNA, for example in bacteria into whose plasmids the DNA has been introduced. It is favorable to now produce several tens of different types of foreign protein for the experimental selection of probe substances to determine the enzyme activity even though only around two to five probe substances are used for a diagnostic method which is subsequently applied.

After being produced, these foreign proteins are masked at both ends with protective groups and provided with covalently bound biotin groups close to the ends, or at least close to one end. The masking protects them from being attacked by exopeptidases; the biotin groups mean that the digest peptides, if they still carry biotin groups, can easily be extracted subsequently by being reversibly bound to immobilized streptavidin. Biotin is a non-protein substance (molecular weight 244.3 Daltons). The specialist is familiar with the method of binding biotin to proteins.

Streptavidin is a protein with a molecular weight of 50 to 60 kilodaltons which very specifically binds the biotin and the digest products which are covalently bound with the biotin. Streptavidin can be covalently bound to surfaces of solids, as the specialist is also aware. Micro-titration plates with streptavidin coatings of the inside surfaces of the micro-vessels are commercially available, for example.

To experimentally determine their suitability, a selection of ten to thirty such probe substances are now added to blood serum samples from a cohort of patients with defined known diseases and to reference blood serum samples from a cohort of healthy people, and all incubated under the same conditions. The reaction products are then extracted by surfaces coated with streptavidin. The reaction products are washed in the immobilized state and then separated from the streptavidin with alkaline solution, for example an ammonia solution. The reaction products are prepared together with matrix substance in the familiar way on sample supports and measured in a MALDI time-of-flight mass spectrometer. The method can be optimized by varying the addition and incubation conditions. By varying the probe substances, those probe substances are identified which produce a significant difference in the nature and intensity of the reaction products between the cohorts of different types of blood samples.

The reaction products can be extracted by immobilization on the interior walls of the micro-vessels of micro-titration plates or in pipettes, but also on the surfaces of added particles.

Particularly suitable are small magnetic beads which can be drawn through the solution or held on the wall by suitable magnets. Automatic pipetting devices for automatically handling solutions with suspensions of small magnetic beads are commercially available.

To evaluate the mass spectra of the reaction products in samples from cohorts of precisely documented patients, computer programs are commercially available which generally use statistical methods to work out significantly different patterns. To use this invention to maximum effect, these programs can be supplemented with program sections which can identify the digestion ladders from cut-out fragments of the probe substances. By applying these programs to mass spectra obtained by adding different types of probe substances using different method parameters, the method can be optimized in the usual way for determining disease-specific enzyme activities.

Once such a method of determining disease-specific enzyme activities has been developed and optimized on the basis of the reaction product patterns, the method can be applied to the measurement of the enzyme activities with the optimum probe substances and the optimum method parameters. Comparative measurements of enzyme activities are used in many fields of medical and biological research. If these measurements are to be used for diagnostic purposes, and if these diagnostic measurements are to be applied across the board in several laboratories, then, in Europe, the method has to be validated according to the IVD Directives. In the USA, it has to be validated by the FDA (Food and Drug Administration).

After such a method has been validated, it can be used widely and is not tied to an individual laboratory and so to the responsibility of the laboratory doctor. Thus, for example, standardized and ready made vessels can be used to take the blood, produce the serum by centrifuging the blood after it has coagulated, incubate it and carry out the broadband extraction and washing of the immobilized reaction products, all in the doctor's practice where the blood is taken. The standardized vessels are equipped with identifiers for unambiguous identifications. The identifiers can consist of printed barcodes, adhesive printed tags made of paper or plastic with barcodes or other information, or chips with electronically readable information (RFID=radio frequency identification).

The vessels with the immobilized reaction products can now be sent to the mass spectrometry laboratory. Depending on the method specification, the washing liquid put into the vessels last can remain there, the vessels can be filled with a special transportation fluid which also comes ready-made, or the specially drained vessel, moist or dried, also preferably filled with inert gas, can be sent off. The washing or transportation liquid can contain antibiotic substances, for example sodium azide.

In the mass spectrometry laboratory, the reversibly immobilized reaction products can be removed from the immobilization vessel simply by taking them up with a few microliters of a suitable liquid, for example a strong organic solvent such as acetonitrile or methanol, or with an ammoniac solution, and can be placed onto the mass spectrometric sample support. The reaction products of probe substances whose anchor groups were appended by means of chemolytically or photolytically cleavable linkers can be released by cleaving the linkers. The quantity of solvent used to absorb the reaction products is not critical since it will subsequently be evaporated. The solvent here can be provided with a matrix substance, as is required for ionization in the MALDI mass spectrometer, at this stage. Alternatively, the matrix substance can be already on the sample support or be added afterwards. This process can easily be automated. It is also simple to read out a barcode identifier located on the immobilization vessel so that sample mix-ups can be excluded as far as possible.

The mass spectrometers used can have MALDI ion sources or electrospray ion sources (ESI). If a MALDI mass spectrometer is used, the eluate taken from the immobilization vessel is mixed with a suitable matrix and dried on a sample support. The solid sample on the sample support is then bombarded with flashes of laser light in the ion source of the mass spectrometer; the ions created are separated according to their mass by means of their time of flight in the time-of-flight mass spectrometer; they are then detected in an ion detector and measured according to their quantity. This process of ionization using matrix-assisted laser desorption (MALDI) provides only singly charged, intact ions of the molecules; the mass spectrum is thus a true representation of the profile of the extracted reaction products. The eluate can be fed into a mass spectrometer with electrospray ion source (ESI) either directly or separated again by a chromatograph. This type of ionization also supplies multiply charged ions of the analyte molecules, however; the mass spectrum is therefore more difficult to analyze. It is for this reason that MALDI mass spectrometry is generally preferred for scanning protein profiles.

The methods of searching for biomarkers briefly described here for the procedure for determining the enzyme activities in blood according to the invention and the application methods derived therefrom for use in diagnostics or research can be modified in a number of ways.

If, for example, the enzymatic reaction is very fast and very homogeneous, then it is possible that instead of a long digestion ladder only digest fragments of roughly the same length are found, i.e. only a short intermediate stage of a steadily progressing breakdown is visible in the mass spectra. In this case, it is expedient to not add the probe substance all at once but to add it over a period of time. It is then possible to measure the different types of intermediate states at the same time in a mass spectrum; this makes it easier to detect the digestion ladders. Pipetting robots can be used to spread the addition over a period of time. It is also possible, however, to keep the probe substances in special vessels so that they are only given up to an added liquid as time goes on, for example by gradual dissolution or membrane diffusion.

Some enzymes cannot work well, if at all, without additional auxiliary substances which form so-called coenzymes with the enzymes. Many enzymatic reactions are brought about by such coenzymes. The auxiliary substances for forming such coenzymes are known for many enzymes. They can likewise be added to improve the work of the enzymes. This generally requires only minute amounts since the enzyme complexes formed continue to be only catalytically effective. The auxiliary substances for the coenzymes are therefore not used up.

Other enzymes are only involved in the removal or modification of side chains, for example phosphorylations or sulfations. In this case, the foreign proteins used as probe substances can carry such side chains.

If biotin groups are bound to the foreign proteins close to the N- or C-terminal ends, then the digestion by the exopeptidases must be prevented from extending beyond the amino acids to which these biotin groups are attached. It is possible to incorporate artificial amino acids into the foreign proteins in order to interrupt the breakdown at this point. It is thus possible to halt every breakdown of a peptide at a predetermined minimum length. This is favorable for mass spectrometric detection, where measurements of short peptides of any length are frequently only possible with great difficulty.

Instead of biotin, other chemical groups can also be used as the anchor groups. If these anchor groups do not bind reversibly to the immobilized capture substances used, then the anchor groups can be bound to the probe substances via cleavable linkers. Many types of such linkers are known. Photolytically cleavable linkers, which can be irreversibly cleaved without the addition of chemicals under a UV lamp, are particularly convenient. It is also possible to use chemically, thermally or enzymatically cleavable linkers.

The coatings with which the broadband extractions are undertaken, and especially the coatings with capture substances, can be located on the interior surfaces of vessels, on filter material with various types of structure—such as felts, nonwovens or open-pored solid foams—or on the surfaces of macroscopic or microscopic packing pellets. Microscopic packing pellets can be present in the form of stable suspensions. Small magnetic beads are particularly suitable here since they can be moved through the liquid with magnets. They can be held fast to the walls of the vessel, for example, in order to exchange blood serum for washing liquid after the reaction products have been immobilized. Automatic pipetting devices which contain devices for treating liquids with magnetizable microparticles are commercially available.

The particle accumulations adhering to the wall or sedimented are then freed from the sample solution by draining or pipetting, and a washing liquid is added. The particles are washed by removing the magnet and by stirring. The stirring can also be brought about by magnetic forces. The washing process can be repeated several times where necessary. Finally, an eluting fluid is added to the accumulated particles, which are now largely free of liquid, to separate the proteins from the antibodies or the other types of capture molecule. These eluting fluids are generally strong polar organic solvents such as acetone, acetonitrile or alcohols. The eluting fluids with the proteins are then fed to the mass spectrometric measurement.

Instead of using magnetic forces to sediment the particles, particles with immobilized proteins can also be simply filtered out and washed by filtration on filter paper or frit.

Packing pellets with different shapes or colors can even be equipped with different types of layers to extract different protein profiles. These can include actively binding surfaces for the extraction of globulins and albumins which bring about a depletion of these highly concentrated proteins.

The extraction can also be brought about by binding specific sequence motifs of the reaction products to corresponding capture motifs of capture substances. The probe substances themselves are already tailored in such a way that they contain these sequence motifs and that these sequence motifs preferably do not fall victim to the enzymatic breakdown. Various types of bonds of peptide sequence motifs to other substances, for example to DNA sequences, have been elucidated.

For good quantitative evaluation it is favorable to add not only the decomposable probe substances to the blood samples, but also non-decomposable reference substances at a known concentration. These can then serve as a concentration reference in the mass spectrometric measurement.

Methods according to this invention can be used for a wide variety of analyses. In medical research, it is possible to study the catalytic activity of enzymes in blood in general, under different conditions on different substrates. In pharmacological R & D, the effectiveness of pharmacological active substances can be investigated. The methods can be used to search for or develop favorable probe substances. The dosage of drugs can be optimized. Finally, it is possible to diagnose diseases or metabolic anomalies if they are linked to the occurrence of enzymes which work in a specific way.

With knowledge of this invention, those skilled in the art can develop further embodiments of the method. All these embodiments should be included in the idea of the invention.

We claim:

1. A method for determining enzyme activities in blood, the method comprising the steps of:
    a) providing whole blood, plasma or serum with active enzymes;
    b) adding specified quantities of one or more exogoenous proteins;
    c) incubating the whole blood, plasma or serum for a specified time under specified conditions, wherein the added exogenous proteins are exposed to enzymatic activity;
    d) extracting at least one reaction product produced from the exogenous proteins by the enzymatic activity; and
    e) measuring extracted reaction products by mass spectrometry, wherein the exogenous proteins are masked at the C terminus, at the N terminus or at both termini in such a way that they are not broken down by exopeptidases of the whole blood, plasma or serum.

2. The method of claim 1, wherein structures of the exogenous proteins added in step b) are known.

3. The method of claim 1, wherein the exogenous proteins added in step b) are not added all at once but spread over time, so that steps b) and c) temporally overlap.

4. The method of claim 1, wherein the exogenous proteins added in step b) are equipped with anchor groups which serve to immobilize some reaction products on capture substances in step d).

5. The method of claim 4, wherein the anchor groups are bound to the exogenous proteins by cleavable linkers.

6. The method of claim 5, wherein the linkers are chemolytically, enzymatically, thermally or photolyticaily cleavable.

7. The method of claim 4, wherein biotin is used as an anchor group and streptavidin as a capture substance.

8. The method of claim 1, wherein the exogenous proteins contain sequence patterns which enable cleavage by endopeptidases.

9. The method of claim 1, wherein the exogenous proteins contain sequence patterns which enable a specific binding to capture substances and hence a specific extraction.

10. The method of claim 1, wherein the exogenous proteins contain sequence patterns which are particularly suitable for broadband extraction with reversed phases.

11. The method of claim 1, wherein reaction products of the exogenous proteins added in step b) are extracted at step d) by broadband extraction by reversible immobilization on hydrophobic coatings, on coatings with anion or cation exchangers, on stably bound metals of different types or on coatings with stably bound antibodies.

12. The method of claim 1, wherein, for quantitative determinations, one or more reference substances which can be extracted but which are not enzymatically broken down in the whole blood, the plasma or the serum are added to the whole blood, the plasma or the serum in addition to the exogenous proteins added in step b).

13. The method of claim 1, wherein auxiliary substances are added to the whole blood, the plasma or the serum in addition to the exogenous proteins added in step b), said auxiliary substances affecting the activity of the enzymes.

14. The method according to claim 1, wherein the enzyme activities of a blood sample is determined and compared in order to diagnose a disease.

15. The method according to claim 1, wherein the enzyme activities of a blood sample is determined and compared in order to determine a metabolic anomaly.

16. The method according to claim 1, wherein the enzyme activities of a blood sample is determined and compared in order to determine the effectiveness of a pharmacologically active substance.

17. The method of claim 1, wherein the extraction in step (d) is done by reversed phase chromatography.

18. The method of claim 1, wherein artificial amino acids are incorporated in the exogenous proteins.

19. A method for identifying biomarkers, the method comprising the steps of:
    a) providing blood samples from a cohort of patients and from a cohort of healthy people;
    b) adding specified quantities of a plurality of different exogenous proteins to the samples;
    c) incubating the samples for a specified time under specified conditions;
    d) extracting reaction products produced from the exogenous proteins by enzymatic activity in the samples;
    e) measuring extracted reaction products by mass spectrometry; and
    f) identifying those exogenous proteins as biomarkers, which produce a significant difference in the corresponding reaction products comparing both cohorts, wherein the exogenous proteins are masked at the C terminus, at the N terminus or at both termini in such a way that they are not broken down by exopeptidases of the whole blood, plasma or serum, and wherein the exogenous proteins are equipped with anchor groups which serve to immobilize some reaction products on capture substances in step d).

20. A method for determining enzyme activities in blood, the method comprising the steps of:
    a) providing whole blood, plasma or serum with active enzymes;
    b) adding specified quantities of one or more types of exogenous proteins;

c) incubating the whole blood, plasma or serum for a specified time under specified conditions, wherein the added exogenous proteins are exposed to enzymatic activity;

d) extracting at least one reaction product produced from the exogenous proteins by the enzymatic activity; and e) measuring extracted reaction products by mass spectrometry, wherein artificial amino acids are incorporated in the exogenous proteins.

* * * * *